United States Patent
Liu

(10) Patent No.: US 9,301,549 B2
(45) Date of Patent: Apr. 5, 2016

(54) ELECTRONIC CIGARETTE DEVICE, ELECTRONIC CIGARETTE AND ATOMIZATION DEVICE THEREOF

(71) Applicant: Qiuming Liu, Shenzhen (CN)

(72) Inventor: Qiuming Liu, Shenzhen (CN)

(73) Assignee: HUIZHOU KIMREE TECHNOLOGY CO., LTD., SHENZHEN BRANCH, Shenzhen, Guangdong Province (CN)

( * ) Notice: Subject to any disclaimer, the term of this patent is extended or adjusted under 35 U.S.C. 154(b) by 272 days.

(21) Appl. No.: 13/882,738

(22) PCT Filed: Jan. 8, 2013

(86) PCT No.: PCT/CN2013/070201
§ 371 (c)(1),
(2) Date: Apr. 30, 2013

(87) PCT Pub. No.: WO2014/107837
PCT Pub. Date: Jul. 17, 2014

(65) Prior Publication Data
US 2014/0190478 A1 Jul. 10, 2014

(51) Int. Cl.
*A24F 47/00* (2006.01)
*A61M 15/06* (2006.01)

(52) U.S. Cl.
CPC ............ *A24F 47/008* (2013.01); *A24F 47/002* (2013.01); *A61M 15/06* (2013.01)

(58) Field of Classification Search
CPC .......... A61M 15/0015; A61M 11/042; A61M 2205/8206; A61M 15/06; A61M 2205/3653; A61M 15/0025; A61M 11/04; A61M 11/041; A61M 15/0065; A61M 16/10; A61M 11/001; A61M 15/0023; A61M 15/025; A24F 47/008; A24F 47/002; A24F 13/00; A24F 47/00; A24F 47/004; H05B 3/03; H05B 3/22; B05B 17/0607; A61B 18/04; A61B 18/044; A61B 18/046; A61B 18/048

USPC ............ 128/200.11, 200.12, 200.14, 200.16, 128/200.18, 200.24, 202.21, 202.27, 128/203.12, 203.15, 203.25–203.27, 128/204.13; 131/194, 270–273, 329, 360; 239/135, 136; 290/1 A, 1 R

See application file for complete search history.

(56) References Cited

U.S. PATENT DOCUMENTS

| | | | |
|---|---|---|---|
| 2011/0036346 A1* | 2/2011 | Cohen et al. | 128/200.14 |
| 2011/0303231 A1* | 12/2011 | Li et al. | 131/329 |
| 2012/0111347 A1* | 5/2012 | Hon | 131/329 |
| 2013/0220315 A1* | 8/2013 | Conley et al. | 128/202.21 |

* cited by examiner

*Primary Examiner* — Jason Flick
*Assistant Examiner* — Elliot S Ruddie
(74) *Attorney, Agent, or Firm* — Cheng-Ju Chiang

(57) ABSTRACT

An electronic cigarette atomization device includes an atomization bushing, an electric heater coil and an atomization base located in the atomization bushing. The atomization device further includes a liquid supply component inserted into the atomization bushing; the liquid supply component is formed by high temperature resistant fiber free of glass fiber and, a through hole axially extended is defined in the middle portion of the liquid supply component; and the electric heater coil is positioned in the through hole of the liquid supply component and is pressed against an inner wall of the liquid supply component. The liquid supply component of the atomization device is made of high temperature resistant fiber material free of glass fiber, thus making the construction and process simplified, leading to low fabrication cost, and causing no damage to human body.

13 Claims, 8 Drawing Sheets

ELECTRONIC CIGARETTE DEVICE, ELECTRONIC CIGARETTE AND ATOMIZATION DEVICE THEREOF

CROSS REFERENCE TO RELATED APPLICATIONS

The present application is a 35 U.S.C. §371 National Phase conversion of International (PCT) Patent Application No. PCT/CN2013/070201, filed on Jan. 8, 2013, the disclosure of which is incorporated by reference herein. The PCT International Patent Application was filed in Chinese.

FIELD OF THE INVENTION

The present invention relates to field of electronic cigarette and cigar case and more particularly, relates to an electronic cigarette of which the atomization device includes liquid storage and supporting components constructed of fiber material with high temperature resistance and free of glass fiber, and an electronic cigarette device thereof.

BACKGROUND OF THE INVENTION

Currently, an electronic cigarette normally is composed of an atomization device and a power supply device connected with each other. Smoke is produced by heating cigar liquid using the atomization device.

A prior art atomization device contained in an electronic cigarette includes an atomization cup for storage of cigar liquid and an atomizer disposed and secured in the atomization cup for heating the cigar liquid.

A tube made of glass fiber is used as a supporting tube of the atomization cup. High temperature resistant cotton covers the supporting tube and finally, oil storage cotton covers the high temperature resistant cotton. As for a prior art atomization cup, the supporting tube, high temperature resistant cotton and oil storage cotton are made of different materials and they are required to be coaxial during manufacture process, the entire process is complicated and high manufacture cost occurs.

The atomizer is disposed and held in the atomization cup and is constructed of an electric heater coil and an atomization stem. The atomization stem serves to support and hold the electric heater coil inside the atomization cup and to guide liquid. The electric heater coil is enwound on the atomization stem for generating smoke by atomization of the cigar liquid. The atomization stem of a conventional atomization device is formed by glass fiber material and as such, a great deal of glass fiber particulate is produced during heating and using process. The particulates will be inhaled in body of the user when the user uses the electronic cigarette, thus causing damage to health.

SUMMARY OF THE INVENTION

One technical problem to be solved by the invention is to provide an electronic cigarette atomization device which employs high temperature resistant fiber material free of glass fiber to form the liquid supply component, thus making the construction and process simplified, leading to low fabrication cost, and causing no damage to human body.

Another technical problem to be solved by the invention is to provide an electronic cigarette having an atomization device with simple construction and production process and low cost.

A yet another technical problem to be solved by the invention is to provide an electronic cigarette device having an electronic cigarette which contains an atomization device with simple construction and production process and low cost.

To solve the above problems, the present invention proposes an electronic cigarette atomization device includes an atomization bushing, an electric heater coil and an atomization base located in the atomization bushing. Here, the atomization device further includes a liquid supply component inserted into the atomization bushing. The liquid supply component is formed by high temperature resistant fiber free of glass fiber and, a through hole axially extended is defined in the middle portion of the liquid supply component. The electric heater coil is positioned in the through hole of the liquid supply component and is pressed against an inner wall of the liquid supply component.

Furthermore, the liquid supply component is made of any one of the following fiber materials: non-woven fabrics, wood pulp fiber, chemical fiber, or polyvinyl alcohol.

Moreover, the electric heater coil is a hollow spiral tube and is axially disposed in the through hole.

Furthermore, the middle portion of the electric heater coil is bent many times in turn such that fence construction with arcuation conformable to internal contour of the through hole is formed for sufficiently contacting the inner wall of liquid supply component.

Furthermore, a first and second wire guiding holes for passing through two ends of the electric heater coil are defined in the atomization base.

Further, a first end of the electric heater coil passes through the through hole along a direction toward the atomization base and then passes through the first wire guiding hole; and the second end thereof passes through the through hole along a direction toward an atomization case. Then, the second end is bent and passes through the second wire guiding hole via the outer wall of the liquid supply component.

Furthermore, the atomization base is secured at one end of the liquid supply component. The atomization device further includes an atomization case disposed at the other end of the liquid supply component distanced away from the atomization base for engaging the atomization base to sealably secure the component in the atomization case of the atomization bushing. The atomization base and atomization case have a first and second venting holes respectively defined at their middle portions and communicating with the through hole.

To solve above technical problems according to another aspect, the present invention further discloses an electronic cigarette including an atomization device and a battery connected electrically to the atomization device so as to supply power to the same. Herein, the atomization device is the one as described above. The battery is disposed on the atomization base at one side away from the liquid supply component.

Furthermore, a first electrode component is disposed between the atomization base and battery. The first electrode component includes a first base body, a first post received in the middle portion of the first base body, and a first insulation bushing located between the first base body and first post. The first base body and first post are coupled with both ends of the electric heater coil so as to form the positive and negative electrodes of the atomization device.

Moreover, a second electrode component matched and connected with the first electrode component is disposed on the battery at a side opposite to the first electrode component. The second electrode component includes a second base body, a second post received in the middle portion of the second base body, and a first insulation bushing located between the second base body and second post. The second base body and second post are coupled with the positive and negative electrodes of the battery.

Furthermore, the electronic cigarette includes an absorption stem and a battery stem connected with the absorption stem. The absorption and battery are detachably connected with each other. The absorption stem and battery stem have a first and second connection portions at their corresponding ends respectively for realizing stable connection between two stems.

Furthermore, the atomization bushing is the absorption stem. The first base body is disposed on the atomization bushing at an end connected with the battery and forms the first connection portion. The second base body is located on the battery stem at an end connected with the absorption stem and forms the second connection portion.

Moreover, the electronic cigarette further includes an atomization control unit electrically coupled with the battery so as to provide power to the atomization device or shut off power provided to the atomization device. The atomization control unit is positioned between the atomization base and battery. Alternatively, it may be positioned on the battery at a side far away from the atomization base.

Furthermore, the atomization control unit includes an atomization control circuit and an atomization control switch connected to the atomization control circuit. The atomization control switch is a capacitive sensor switch, gas flow sensor switch, or button switch. The atomization control circuit is integrated into the atomization control switch. Alternatively, the atomization control unit also includes an atomization control circuit board connected to both of the battery and atomization control switch. The atomization control circuit is integrated into the atomization control circuit board.

To solve a further technical problem as described above, the present invention also discloses an electronic cigarette device including an electronic cigar case and electronic cigarette contained in the cigar case. Here, the electronic cigarette is the one as described above.

The invention has the following technical effects. The liquid supply component is directly made of high temperature fiber material free of glass fiber and as a result, the component functions to store cigar liquid and support and hold the electric heater coil, thus significantly simplifying total construction of the atomization device of a conventional electronic cigarette, leading to simple structure, simple manufacture process, effectively reducing cost, avoiding use of glass fiber, largely improving self-safety of the electronic cigarette, and avoiding causing damage to human body.

The embodiments of the invention are described in detail in conjunction with the accompanying drawings.

DETAILED DESCRIPTION OF THE INVENTION

As shown in FIGS. 1-8, the invention provides an electronic cigarette device including an electronic cigarette 100 and an electronic cigar case 200 for accommodating the former.

Reference is made to FIGS. 4-7. The electronic cigarette 100 contains an atomization device 10 and a battery 20. The atomization device 10 works to transform cigar liquid into smoke to be absorbed by a user. The battery 20 is electrically connected with the atomization device 10 so as to power the atomization device 10.

Figure 1:
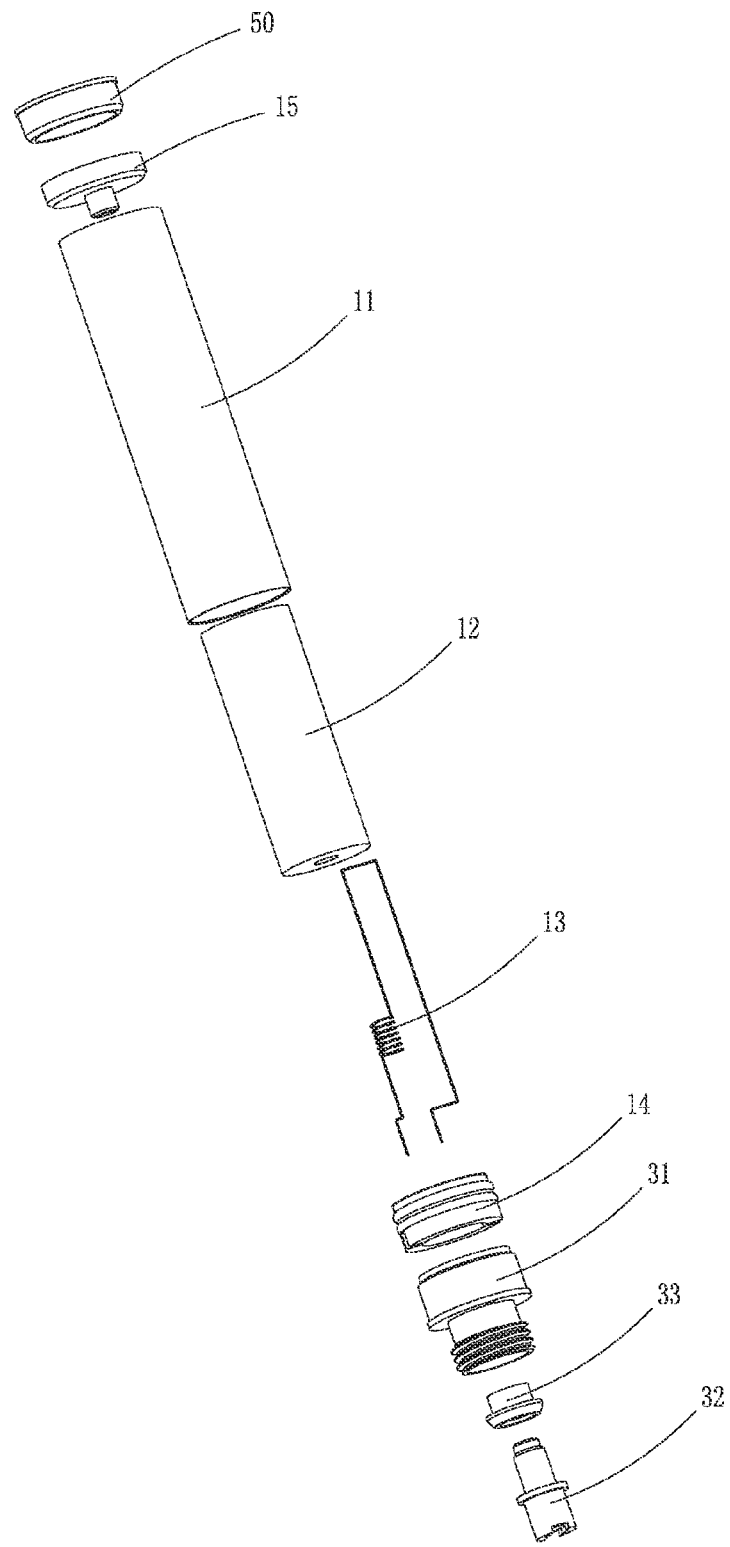
FIG. 1 is an exploded view of an electronic cigarette absorption stem according to an embodiment of the invention.
Figure 2:
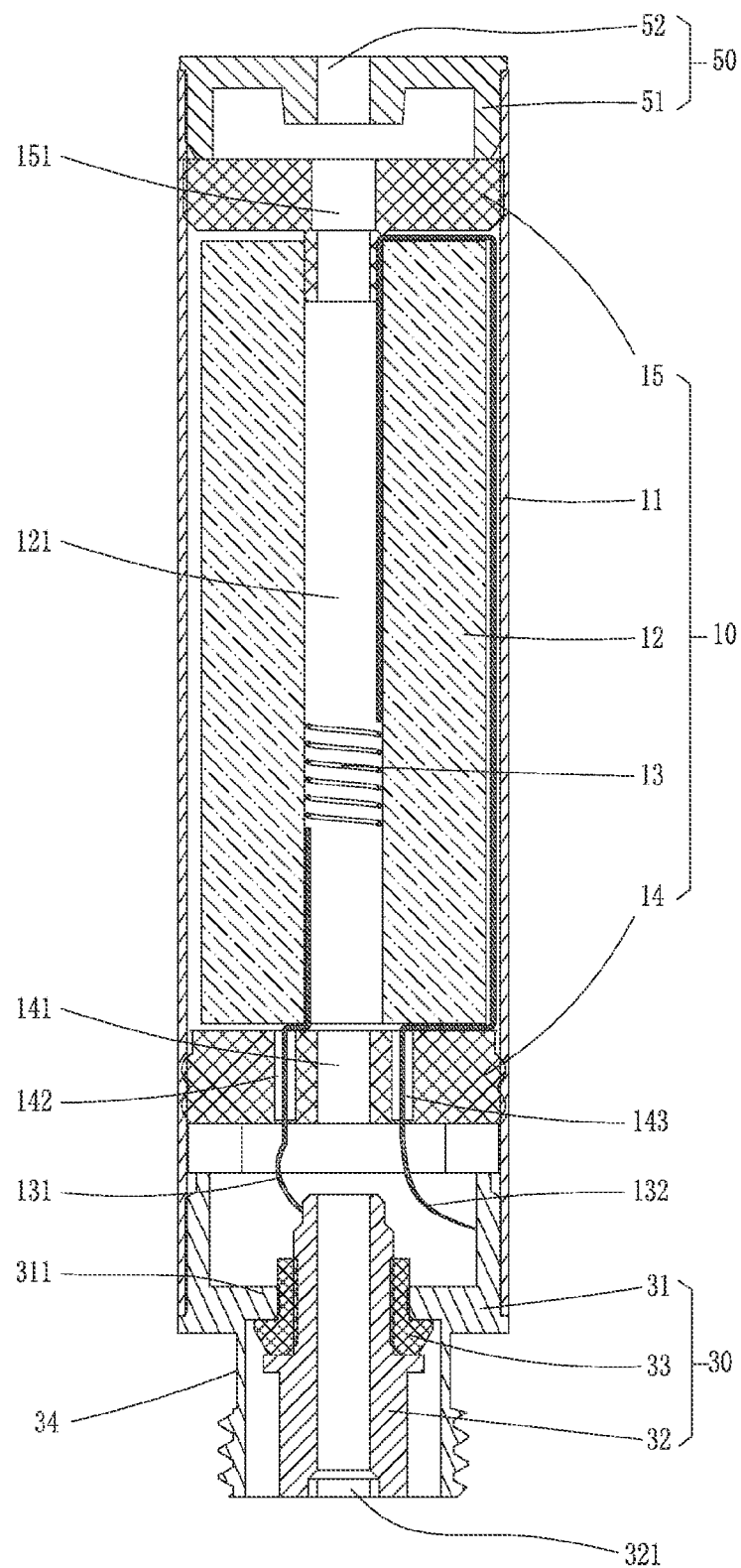
FIG. 2 is a cross-sectional view of an electronic cigarette absorption stem along Line A-A of FIG. 4 according to an embodiment of the invention.

As shown in FIGS. 1-2, the atomization device 10 has an atomization bushing 11, a liquid supply component 12, an electric heater coil 13, an atomization base 14 and an atomization case 15.

The atomization 11 is sleeved on the outer portion of the liquid supply component 12, electric heater coil 13, atomization base 14 and atomization case 15, and provides a cup body for the atomization device 10 for containing and sealing cigar liquid. In this embodiment, the atomization bushing 11 is configured to be a cylindrical tubular construction, and the inside of the bushing 11 is hollow so as to define a receiving cavity for receiving respective internal parts of the atomization device 10. Understandingly, in addition to the cylindrical construction of this embodiment, the atomization bushing 11 may also be configured to have any other tubular construction with a hollow cavity.

The liquid supply component 12 is of a hollow tubular construction matching the atomization bushing 11 and is disposed coaxially with the bushing 11. The liquid supply component 12 is formed with high temperature resistant fiber material free of glass fiber for supporting and holding the electric heater coil 13, and absorbing and storing cigar liquid so that the cigar liquid is atomized later by the electric heater coil 13. In present embodiment, the liquid supply component 12 is particularly made of any one of the fiber materials listed below: non-woven fabrics, wood pulp fiber, chemical fiber, or polyvinyl alcohol.

The liquid supply component 12 has a through hole 121 which is defined in its middle portion and is extended axially. The electric heater coil 13 is received in the through hole 121 of the liquid supply component 12 and is pressed against the inner wall of the liquid supply component 12 such that the electric heater coil 13 will sufficiently contact the cigar liquid.

Referring to FIG. 2, in this embodiment, the middle portion of the electric heater coil 13 functioning to heat and atomize cigar liquid is of a spiral tube configuration and is axially disposed in the through hole 121. The outer diameter of the spiral tube formed at the middle portion of the electric heater coil 13 is slightly larger than the inner diameter of the through hole 121 of the liquid supply component 12. As such, the electric heater coil 13 is supported and held in the through hole 121 by press of the electric heater coil 13 against the inner wall of the liquid supply component 12, and the electric heater coil 13 can sufficiently contact the inner wall of the liquid supply component 12 so that the cigar liquid inside the liquid supply component 12 will contact the electric heater coil 13 thus being atomized by the coil 13 and changed to smoke.

As an embodiment, the middle portion of the electric heater coil 13 for heating and atomizing cigar liquid may be bent repeatedly to form a plane portion which may be bent in entirety again to form arcuation conforming to the internal contour of the through hole 121, and finally a fence sufficiently contacting the inner wall of the liquid supply component 12 is formed.

The atomization base 14 is held at one end of the liquid supply component 12 for supporting and holding the liquid supply component 12 and electric heater coil 13 in the atomization bushing 11. As shown in FIG. 2, in present embodiment, the other end of the liquid supply component 12 away from the atomization base 14 is provided with the atomization case 15. The atomization base 14 and atomization case 15 are disposed at two ends of the liquid supply component 12 respectively so as to cooperate with each other with the purposes of sealing and securing the liquid supply component 12 inside the atomization bushing 11. A first venting hole 141 and a second venting hole 151 communicating the through hole 121 for venting purpose are respectively defined at middle portions of the atomization base 14 and atomization case 15. In this embodiment, the atomization base 14 is constructed of rubber material with certain elastic deformation capability such as silica gel. The external contour of the atomization base 14 conforms to the internal contour of the atomization bushing 11 and preferably there is interference fit between the base 14 and bushing 11. The atomization base 11 is pressed against and held in the atomization bushing 11 by its outer wall, thereby realizing seal connection between the base 14 and bushing 11.

In addition, a first wire guiding hole 142 and a second wire guiding hole 143 are axially defined at a side wall of the atomization base 14 for passing through the two ends of the electric heater coil 13 respectively. As shown in FIG. 2 and in this embodiment, a first end 131 of the electric heater coil 13 passes across the through hole 121 along a direction towards the atomization base 14 and then passes through the first wire guiding hole 142, while the second end 132 of the electric heater coil 13 passes across the through hole 121 along a direction towards the atomization case 15 and then is bent along the outer wall of the liquid supply component 12 and travels across the second wire guiding hole 143.

Figure 5:
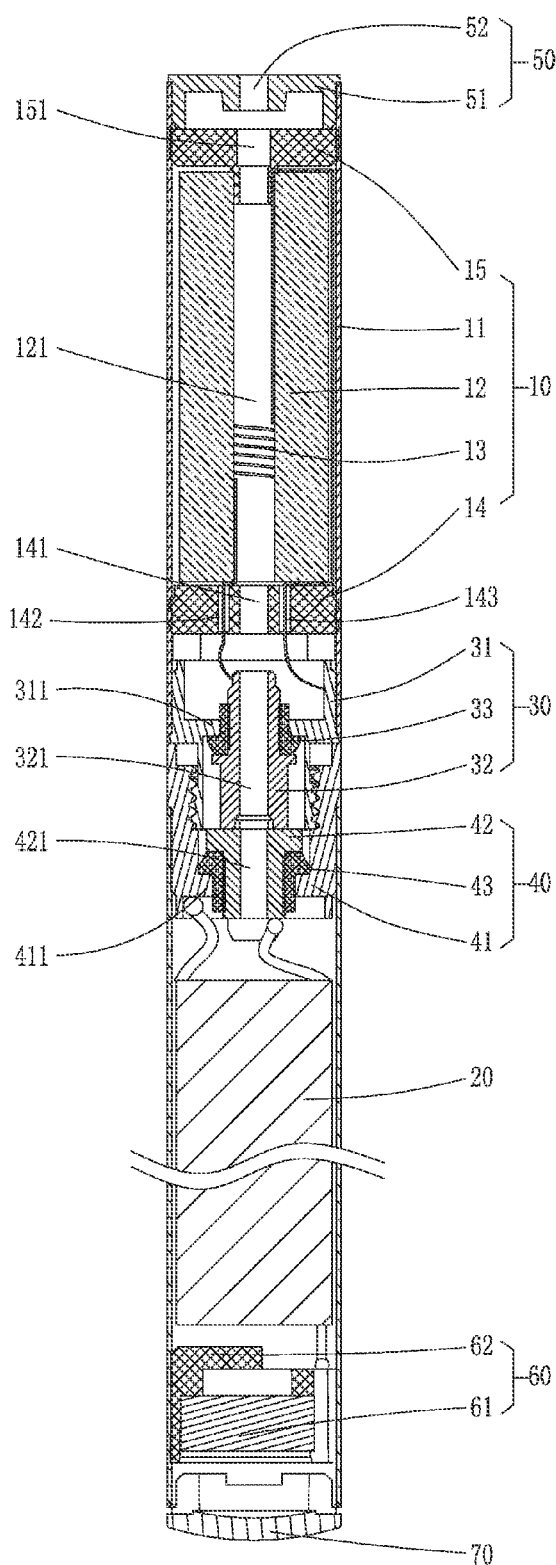
FIG. 5 is a cross-sectional view of an electronic cigarette along Line A-A of FIG. 4 according to a first embodiment of the invention.

Referring to FIG. 5, in present embodiment, the battery 20 is placed on the atomization base 14 at a side away from the liquid supply component 12. A first electrode component 30 is located between the atomization base 14 and battery 20. The first electrode component 30 is connected to two ends of the electric heater coil 13, and is electrically connected as the positive and negative electrodes of the atomization device 10 to the positive and negative electrodes of the battery 20.

Specifically, as shown in FIGS. 1-2 and 5, the first electrode component 30 includes a first base body 31, a first post 32 and a first insulation bushing 33 disposed between the first base body 31 and first post 32. In this embodiment, the first base body 31 and first post are both made of metal conductive material, and are respectively coupled to two ends of the electric heater coil 13 so as to form the positive and negative electrodes of the atomizer 12. The first insulation bushing 33 is made of insulated material for insulating the first base body 31 from the first post 32.

The first base body 31 is of a hollow tube, and a first locking ring 311 for locking the first insulation bushing 33 is extended radially from the inner wall of the first base body 31. The first post 32 is disposed corresponding to the first base body 31, and is locked on the middle portion of the first base body 31 by its first insulation bushing 33 and is insulated from the body 31. In this embodiment, the first post 32 is also of a hollow tube shape, and the middle hollow portion thereof is provided with a first intake hole 321 through which external air may enter into the atomization device 10.

Figure 3:
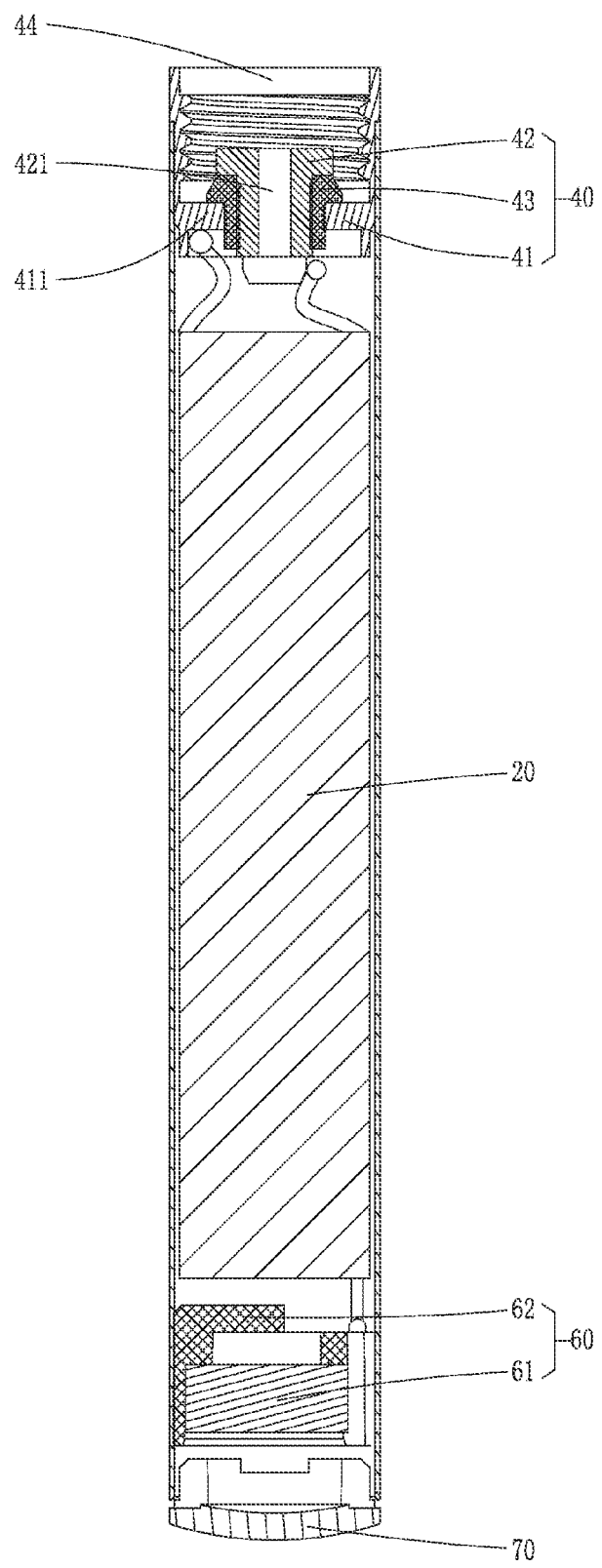
FIG. 3 is a cross-sectional view of an electronic cigarette battery stem along Line B-B of FIG. 4 according to an embodiment of the invention.

Referring to FIGS. 3 and 5, the battery 20 is disposed opposite to the first electrode component 30. A second electrode component 40 is provided on the battery 20 at a side opposite to the first electrode component 30. The second electrode component 40 matches and is connected with the first electrode component 30, thus realizing electrical connection between the battery 20 and atomization device 10.

Specifically, the second electrode component 40 substantially has the same structure as the first electrode component 30, and includes a second base body 41, a second post 42, and a second insulation bushing 43 disposed between the second base body 41 and second post 42 for insulating the second base body 41 from the second post 42. The second base body 41 and second post 42 are connected with the positive and negative electrodes of the battery 20 and atomization device 10 respectively. A second locking ring 411 for locking the second insulation bushing 43 is extended radially from the inner wall of the second base body 41. The second post 42 is disposed corresponding to the second base body 41, and is locked on the middle portion of the second base body 41 by its second insulation bushing 43 and is insulated from the body 41. The second post 4 is also of a hollow tube shape, and the middle portion thereof is provided with a second intake hole 421 communicating the first intake hole 321 for conducting air.

Please refer to FIGS. 2-3 and 5, in this embodiment, one end of the second base body 41 facing the first base body 31 is provided with a holding groove 44 for insertion therein of a corresponding end of the first base body 31, hence holding the first base body 31 in place. One end of the first base body 31 inserted into the second base body 41 is provided with a boss 34. The boss 34 conforms to the internal contour of the holding groove 44 so as to be placed into the holding groove 44. It is understood that as an embodiment, the holding groove 44 may also be defined in the first base body 31, while a corresponding boss 34 is formed on the second base body 41.

When assembling the electronic cigarette 100, the boss 34 of the first base body 31 is placed into the holding groove 44 of the second base body 41 such that the first base body 31 is pressed against the second base body 41, thereby realizing electrical connection between the battery 20 and atomization device 10.

Figure 4:
FIG. 4 is a front view of an electronic cigarette according to a first embodiment of the invention.
Figure 6:
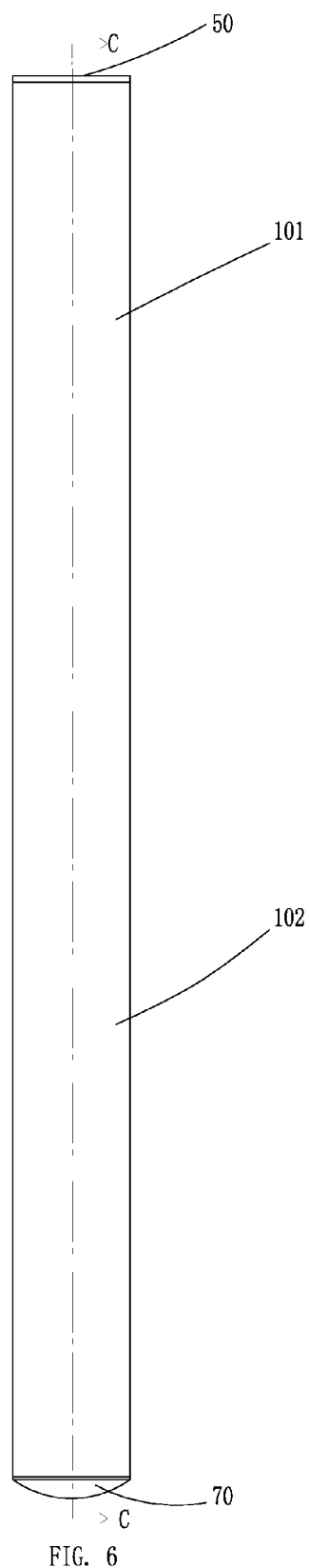
FIG. 6 is a front view of an electronic cigarette according to a second embodiment of the invention.
Figure 7:
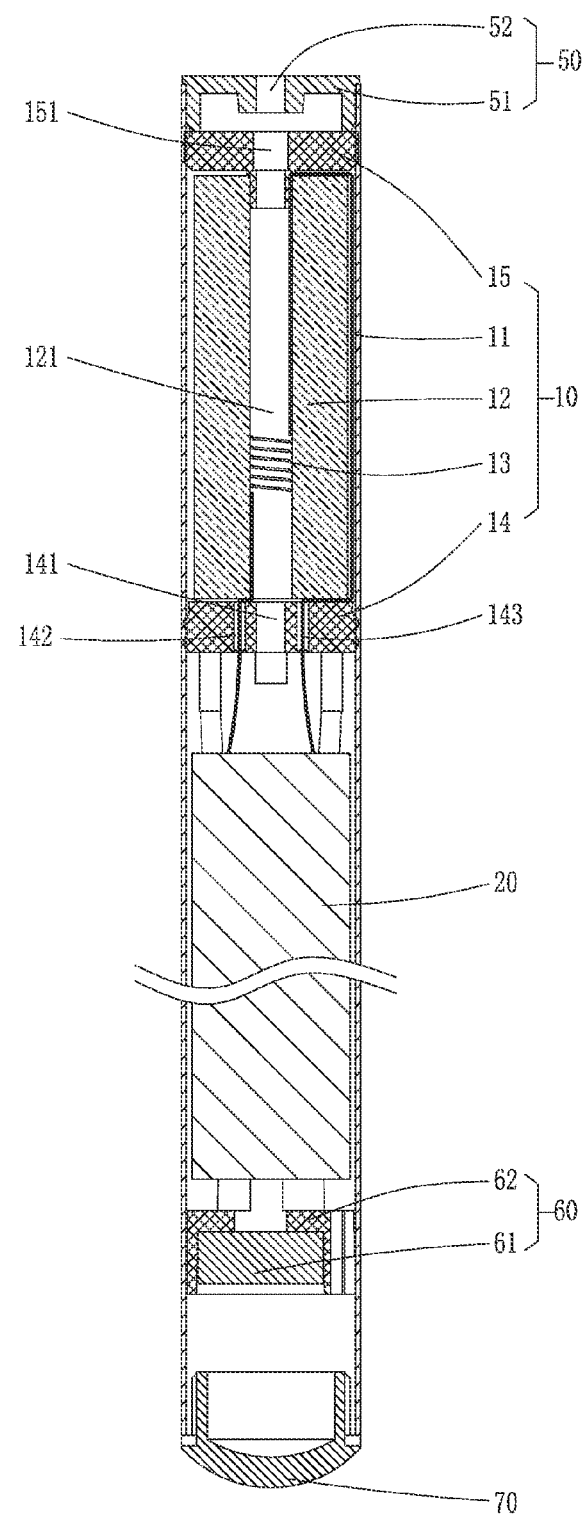
FIG. 7 is a cross-sectional view of an electronic cigarette along Line C-C of FIG. 6 according to a second embodiment of the invention.

Please refer to FIGS. 4-7, one end of the electronic cigarette 100 distanced away from the battery 20 is equipped with a mouthpiece 50. Based on internal components and their functions of the electronic cigarette 100, the outer main stem of the electronic cigarette 100 may be divided into an absorption stem 101 and a battery stem 102. Generally, the absorption stem 101 and battery stem 102 may be configured to have detachable connection as shown in FIGS. 4-5, or to have undetachable integral construction as shown in FIGS. 6-7. In case that the absorption stem 101 and battery stem 102 are configured to have detachable connection, the atomization device 10 is disposed inside the absorption stem 101, and a separate stem body may be provided to the absorption stem 101 so as to receive the entire atomization device 10 in the stem body. Optionally, as shown in FIG. 5, the atomization bushing 11 of the atomization device 10 may work as the stem body of the absorption stem 101. Alternatively, in case that the absorption stem 101 and battery stem 102 are integral with each other, the atomization bushing 11 may also be used as the stem body of the electronic cigarette 100, and the battery 20 and mouthpiece 50 are directly disposed at corresponding two ends of the atomization bushing 11.

Refer to FIGS. 6-7. When the absorption stem 101 and battery stem 102 are configured to have undetachable integral construction, the two ends of the electric heater coil 13 may directly connected with the positive and negative electrodes of the battery 20 without providing the first and second electrode components 30 and 40 between the atomization base 11 and battery 20. Or, there may only be provided with a first electrode component 30 connected to both ends of the electric heater coil 13, and electric connection between the atomization device 10 and battery 20 is achieved by electric connection of the first electrode component 30 to the positive and negative electrodes of the battery 20.

Please refer to FIGS. 4-5. In this embodiment, the absorption stem 101 and battery stem 102 are detachably connected, and the atomization bushing 11 is used as the stem body of the absorption stem 101. The electronic cigarette 100 of the embodiment is described in greater detail.

The corresponding ends of the absorption stem 101 and battery stem 102 are respectively provided with a first connection portion and a second connection portion which are engaged with each other in order that the absorption stem 101 and battery stem 102 are reliably connected together. In present embodiment, the first base body 31 is disposed on the atomization bushing 11 at one end connected to the battery stem 102 and forms the first connection portion. The second base body 41 is disposed on the battery stem 102 at one end connected to the absorption stem 101 and forms the second connection portion. As an embodiment, independent component may also be provided on the corresponding ends of the absorption stem 101 and battery stem 102 so as to form the first and/or second connection portion.

The atomization bushing 11 (that is, the absorption stem 101) may be connected to the battery stem 102 by means of screwing, clasping, insertion, or magnetic adsorption. In this embodiment, the atomization bushing 11 and battery stem 102 are preferably secured together by screwing. Concretely, as shown in FIG. 5, the outer wall of the boss 34 of the first base body is provided with external thread, whereas the inner wall of the holding groove 44 of the second base body is provided with matched internal thread.

As shown in FIGS. 1-7, in this embodiment, the mouthpiece 50 and atomization bushing 11 are separately configured. The mouthpiece 50 includes a nozzle case 51 sleeved on the end portion of the atomization bushing 11 and a suction hole axially defined in the middle portion of the nozzle case 51. As an embodiment, the mouthpiece 50 may be integrally formed with the atomization bushing 11. In present embodiment, the mouthpiece 50 is configured to be a cylindrical construction. It is understood that the mouthpiece 50 may also have tubular construction such as polygon, ellipse and so on. Alternatively, it may also be designed to be a sleeve construction which has predefined taper and of which the diameter is tapered towards the end portion of the mouthpiece 50.

As shown in FIGS. 5 and 7, the electronic cigarette 100 also includes an atomization control unit 60 connected electrically to the battery 20 and atomization device 10 respectively so as to provide power to the device 10 or shut off power supplied to the device 10. The atomization control unit 60 may be disposed between the atomization base 11 and battery 20, or disposed on the battery 20 at a side away from the atomization base 11.

In this embodiment, the atomization control unit 60 is preferably disposed on the battery 20 at a side away from the atomization base 11. The atomization control unit 60 includes an atomization control circuit and an atomization control switch connected with the atomization control circuit.

In this embodiment, the atomization control switch is a sensor switch 61 secured in the battery stem 102 by a switch holding base 62. More specifically, the sensor switch 61 is a capacitive sensor switch. When the electronic cigarette 100 is being used by a user, the capacitive sensor switch senses the capacitance change caused by incoming gas flow and then the switch controls the atomization control circuit to switch on a power supply, thus making the electronic cigarette entering into working status. As an embodiment, the sensor switch 61 may also be a gas flow sensor switch. When the user inhales gas by the mouthpiece 50, negative pressure is generated inside the cavity of the electronic cigarette 100 and in turn, the gas flow sensor switch generates pulse signals to control the atomization control circuit to switch on a power supply.

As the sensor switch 61 in itself is precisely fabricated and generally, a dedicated controller is built therein, the atomization control circuit of this embodiment may be directly integrated into the controller of the sensor switch 61. As an implementation manner, the atomization control circuit may also be integrated into an atomization control circuit board separately disposed outside of the sensor switch 61 and electrically connected to both of the sensor switch 61 and battery 20.

As an implementation manner, the atomization control switch may also be a conventional switch of button type. The button switch is electrically connected to the battery 20 through a button control circuit board such that the atomization control circuit is controlled by pressing the buttons, thus realizing switching on and off of the atomization device 10.

Please refer to FIGS. 3-7, a light emitting device is disposed on the electronic cigarette 100 at the other end away from the mouthpiece 50. The light emitting device is used as a working indicator light of the electronic cigarette 100, and includes a light emitting unit electrically connected to the battery 20 and a light cap 70 disposed at a corresponding end of the battery stem 102. The light cap 70 helps to radiate light generated by the light emitting unit. In this embodiment, the light emitting unit is configured to be a red lamp such that when the smoker smokes the electronic cigarette 100, one end of the electronic cigarette 100 away from the mouthpiece 50 will generate red smoke circles like those produced when a cigar is burned, hence enhancing visual effects of the smoker.

Below, one end of the battery 20 electrically connected to the second post 42 is defined as a positive electrode, while the other end thereof electrically connected to the second base body 41 is defined as a negative electrode. In addition, the atomization control switch is configured to be a sensor switch 61. The current flow routing of the electronic cigarette 100 is described in detail.

When the smoker smokes the electronic cigarette 100, the sensor switch 61 will sense and switch on the atomization control circuit. The detailed current flowing path is as below: the current arrives at the second post 42 from the positive electrode of the battery 20, then travels to the positive electrode of the electric heater coil 121 via the first post 32, next flows to the first base body 31 via the negative electrode of the electric heater coil 121 and finally, comes back to the negative electrode of the battery 20 through the second base body 41.

Understandingly, the electronic cigarette 100 is not limited to the embodiments shown in FIGS. 1-7. Rather, individual features of these embodiments may be combined with each other to form new embodiments.

Figure 8:
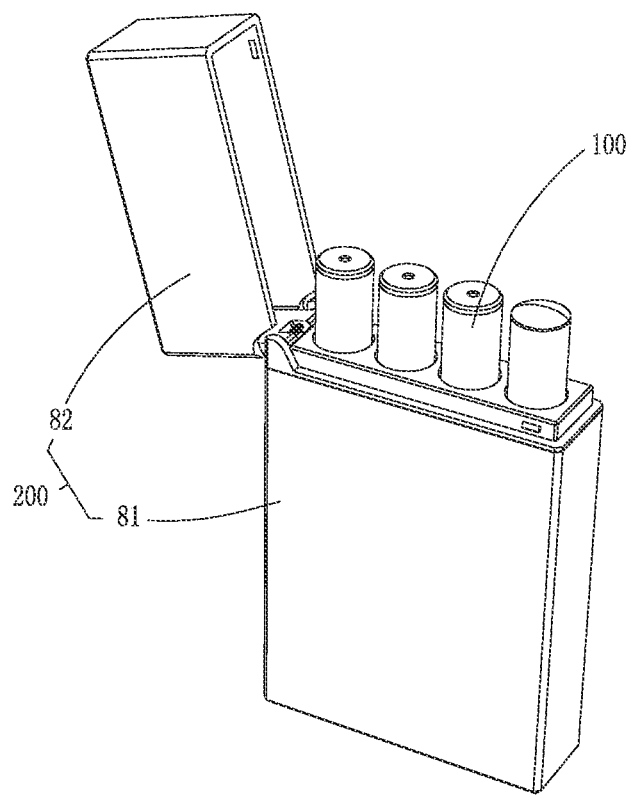
FIG. 8 is a perspective view of an electronic cigarette according to an embodiment of the invention.

As shown in FIG. 8, the electronic cigarette 100 is in general contained in the electronic cigar case 200. The cigar case 200 includes a bottom box 81 for containing therein the electronic cigarette 100 and a case lid 82 covered on the bottom box 81. The bottom box 81 is of a square enclosure and of course, it is not limited to square. Rather, it may also take on circle, ellipse, polygon and the like so long as the case lid 82 will match it when the case lid 82 is installed.

Though various embodiments of the invention have been illustrated above, a person of ordinary skill in the art will understand that, variations and improvements made upon the illustrative embodiments fall within the scope of the invention, and the scope of the invention is only limited by the accompanying claims and their equivalents.

What is claimed is:

1. An electronic cigarette atomization device, comprising an atomization bushing, an electric heater coil and an atomization base located in the atomization bushing, wherein the atomization device further comprises a liquid supply component inserted into the atomization bushing; the liquid supply component is formed by high temperature resistant fiber free of glass fiber and, a through hole axially extended is defined in the middle portion of the liquid supply component; and the electric heater coil is positioned in the through hole of the liquid supply component and is pressed against an inner wall of the liquid supply component;

wherein a first and second wire guiding holes for passing through two ends of the electric heater coil are defined axially in the atomization base; and a first end of the electric heater coil passes through the through hole along a direction toward the atomization base and then passes through the first wire guiding hole; and the second end thereof passes through the through hole along a direction toward an atomization case; the second end is bent and passes through the second wire guiding hole via the outer wall of the liquid supply component.

2. The electronic cigarette atomization device as recited in claim 1, wherein the liquid supply component is made of any one of the following fiber materials: non-woven fabrics, wood pulp fiber, chemical fiber, or polyvinyl alcohol.

3. The electronic cigarette atomization device as recited in claim 1, wherein the electric heater coil is a hollow spiral tube and is axially disposed in the through hole.

4. The electronic cigarette atomization device as recited in claim 1, wherein the middle portion of the electric heater coil is bent many times in turn such that fence construction with arcuation conformable to internal contour of the through hole is formed for sufficiently contacting the inner wall of liquid supply component.

5. The electronic cigarette atomization device as recited in claim 1, wherein the atomization base is secured at one end of the liquid supply component; the atomization device further includes an atomization case disposed at the other end of the liquid supply component distanced away from the atomization base for engaging the atomization base to sealably secure the component in the atomization case of the atomization bushing; and the atomization base and atomization case have a first and second venting holes respectively defined at their middle portions and communicating with the through hole.

6. An electronic cigarette comprising an atomization device and a battery connected electrically to the atomization device so as to supply power to the same, wherein the atomization device is the one as recited in claim 1; and the battery is disposed on the atomization base at one side away from the liquid supply component.

7. The electronic cigarette as recited in claim 6, wherein a first electrode component is disposed between the atomization base and battery; the first electrode component includes a first base body, a first post received in the middle portion of the first base body, and a first insulation bushing located between the first base body and first post; and the first base body and first post are coupled with both ends of the electric heater coil so as to form the positive and negative electrodes of the atomization device.

8. The electronic cigarette as recited in claim 7, wherein a second electrode component matched and connected with the first electrode component is disposed on the battery at a side opposite to the first electrode component; the second electrode component includes a second base body, a second post received in the middle portion of the second base body, and a first insulation bushing located between the second base body and second post; and the second base body and second post are coupled with the positive and negative electrodes of the battery.

9. The electronic cigarette as recited in claim 8, wherein the electronic cigarette includes an absorption stem and a battery stem connected with the absorption stem; the absorption and battery are detachably connected with each other; and the absorption stem and battery stem have a first and second connection portions at their corresponding ends respectively for realizing stable connection between two stems.

10. The electronic cigarette as recited in claim 9, wherein the atomization bushing is the absorption stem; the first base body is disposed on the atomization bushing at an end connected with the battery and forms the first connection portion; and the second base body is located on the battery stem at an end connected with the absorption stem and forms the second connection portion.

11. The electronic cigarette as recited in claim 6, wherein the electronic cigarette further includes an atomization control unit electrically coupled with the battery so as to provide power to the atomization device or shut off power provided to the atomization device; the atomization control unit is positioned between the atomization base and battery; alternatively, it is positioned on the battery at a side far away from the atomization base.

12. The electronic cigarette as recited in claim 11, wherein the atomization control unit includes an atomization control circuit and an atomization control switch connected to the atomization control circuit; the atomization control switch is a capacitive sensor switch, gas flow sensor switch, or button switch; the atomization control circuit is integrated into the atomization control switch; alternatively, the atomization control unit also includes an atomization control circuit board connected to both of the battery and atomization control switch; and the atomization control circuit is integrated into the atomization control circuit board.

13. An electronic cigarette device comprising an electronic cigar case and electronic cigarette contained in the cigar case, wherein the electronic cigarette is the one as recited in claim 6.

* * * * *